United States Patent
Tanaka et al.

(10) Patent No.: US 10,571,999 B2
(45) Date of Patent: Feb. 25, 2020

(54) PROXIMITY BASED AND DATA EXCHANGE AND USER AUTHENTICATION BETWEEN SMART WEARABLE DEVICES

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignees: SONY CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 73 days.

(21) Appl. No.: 15/236,448

(22) Filed: Aug. 14, 2016

(65) Prior Publication Data
US 2017/0012972 A1    Jan. 12, 2017

Related U.S. Application Data

(63) Continuation of application No. PCT/US2015/016676, filed on Feb. 19, 2015.
(Continued)

(51) Int. Cl.
*H04L 29/06* (2006.01)
*G06F 3/01* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC . H04L 63/0861; H04L 63/0869; H04W 12/06
See application file for complete search history.

(56) References Cited

U.S. PATENT DOCUMENTS

| 8,447,329 B2 | 5/2013 | Kadirkamanathan et al. |
| 2003/0046228 A1* | 3/2003 | Berney ............... G06F 21/32 705/41 |

(Continued)

FOREIGN PATENT DOCUMENTS

| CN | 1610920 A | 4/2005 |
| EP | 1 314 102 B1 | 4/2001 |

(Continued)

OTHER PUBLICATIONS

Korean Intellectual Property Office (KIPO), Notice of Preliminary Rejection dated Dec. 13, 2017, Korean patent application No. 10-2016-7021796, p. 1-12, English-language translation, pp. 13-24, claims examined, pp. 25-36.

(Continued)

*Primary Examiner* — Saleh Najjar
*Assistant Examiner* — Devin E Almeida
(74) *Attorney, Agent, or Firm* — O'Banion & Ritchey LLP; John P. O'Banion

(57) ABSTRACT

A system and method including a disposable wearable device that provides enhanced capabilities to a non-wearable device for a limited period of time by sensing proximity and securely exchanging permissions with the non-wearable device. In one embodiment, the wearable device is capable of sensing one or more bio-signals that are provided to the non-wearable, tactile feedback, or the like. The wearable (Continued)

device may be disposable and may also provide additional tactile feedback for the extended feature (e.g. game feedback, etc). In another embodiment, the wearable device is capable of sensing one or more bio-signals that are provided to the non-wearable, tactile feedback, or the like.

12 Claims, 8 Drawing Sheets

Related U.S. Application Data

(60) Provisional application No. 61/943,837, filed on Feb. 24, 2014.

(51) Int. Cl.

| | |
|---|---|
| G06F 1/16 | (2006.01) |
| G06F 1/3206 | (2019.01) |
| G06F 1/3234 | (2019.01) |
| G06F 1/3287 | (2019.01) |
| G06F 19/00 | (2018.01) |
| G16H 40/63 | (2018.01) |
| H04W 12/06 | (2009.01) |
| G16H 40/67 | (2018.01) |
| G08B 7/00 | (2006.01) |

(52) U.S. Cl.
CPC .......... *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/3418* (2013.01); *G16H 40/63* (2018.01); *G16H 40/67* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(56) References Cited

U.S. PATENT DOCUMENTS

| | | | |
|---|---|---|---|
| 2005/0021679 A1 | 1/2005 | Lightman et al. | |
| 2006/0115130 A1* | 6/2006 | Kozlay | G02B 27/0093 |
| | | | 382/117 |
| 2008/0055074 A1* | 3/2008 | Gao | A61B 5/0002 |
| | | | 340/539.13 |
| 2010/0217099 A1* | 8/2010 | LeBoeuf | A61B 5/00 |
| | | | 600/301 |
| 2010/0226346 A1* | 9/2010 | Caldwell | H04M 15/00 |
| | | | 370/338 |
| 2012/0202514 A1 | 8/2012 | Kadirkamanathan et al. | |
| 2012/0223823 A1* | 9/2012 | Dunko | G06F 19/00 |
| | | | 340/407.1 |
| 2012/0316456 A1* | 12/2012 | Rahman | G06F 1/163 |
| | | | 600/547 |
| 2012/0316896 A1* | 12/2012 | Rahman | G06F 19/3418 |
| | | | 705/3 |
| 2013/0111039 A1 | 5/2013 | Gomes | |
| 2013/0165164 A1* | 6/2013 | Rowe | H04N 21/4126 |
| | | | 455/466 |
| 2013/0172691 A1* | 7/2013 | Tran | A61B 8/488 |
| | | | 600/301 |
| 2013/0176142 A1* | 7/2013 | Drysdale | G06F 3/011 |
| | | | 340/870.02 |
| 2013/0198694 A1 | 8/2013 | Rahman et al. | |
| 2013/0290427 A1* | 10/2013 | Proud | G06F 8/65 |
| | | | 709/204 |
| 2014/0085101 A1* | 3/2014 | Rahman | A61B 5/0022 |
| | | | 340/870.01 |
| 2014/0201832 A1 | 7/2014 | Yi et al. | |
| 2015/0205949 A1* | 7/2015 | Iskin | G06F 21/51 |
| | | | 713/187 |

FOREIGN PATENT DOCUMENTS

| | | |
|---|---|---|
| EP | 1314102 B1 | 6/2009 |
| JP | 2002-334032 | 11/2002 |
| JP | 2005-528662 A | 9/2005 |
| JP | 2009-164749 A | 7/2009 |
| JP | 2012-95796 A | 5/2012 |
| KR | 10-2006-0048044 | 5/2006 |
| KR | 10-2008-0103386 A | 11/2008 |
| WO | 2013/073737 A1 | 5/2013 |

OTHER PUBLICATIONS

Japanese Patent Office (JPO), Notification of Reasons for Refusal, related Japanese Patent Application No. P2016-551277 dated Jul. 24, 2017, pp. 1-4, English-language translation, pp. 5-6, claims examined, pp. 7-18. US 2014/0201832 is an English-language equivalent to WO 2013/073737 cited therein.

European Patent Office (EPO), extended European search report dated Sep. 25, 2017, related European application No. 15751850.7, pp. 1-9, with claims searched, pp. 10-12.

United States Patent and Tradmark Office (USPTO), International Search Report and Written Opinion, PCT International Application No. PCT/US2015/016676, dated Jul. 8, 2015, pp. 1-9, with claims searched, pp. 10-21.

State Intellectual Property Office of the People's Republic of China, Notification of the First Office Action dated Mar. 12, 2018, related Chinese patent application No. 201580007378.7, English-language translation pp. 1-10, English-language claims examined pp. 11-22, Chinese-language office action pp. 23-31.

Japan Patent Office (JPO), Preappeal Review Report dated May 18, 2018, related Japanese patent application No. 2016-551277, Japanese language document pp. 1-3, English-language translation pp. 4-6, claims examined pp. 7-21.

Asahi, Yu-Ki et al., "Development of Non-verbal Communications System 'Taion Heart'" NTT DOCOMO, Technical Journal, Japan, the Telecommunications Association, Dec. 27, 2010, vol. 18, No. 4, pp. 61-64.

Korean Intellectual Property Office (KIPO), Notice of Last Preliminary Rejection dated May 29, 2018, related Korean patent application No. 10-2016-7021796, Korean-language document pp. 1-19, English-language translation pp. 20-38, claims examined pp. 39-50.

Japan Patent Office (JPO), Official Action dated Apr. 3, 2019, related Japanese patent application No. 2016-551277, Japanese language document pp. 1-10, English-language concise explanation pp. 11, claims examined pp. 12-25.

European Patent Office (EPO), Communication pursuant to Article 94(3) EPC (office action) dated Jun. 14, 2019, related European patent application No. 15 751 850.7, pp. 1-7, claims examined, pp. 8-11.

* cited by examiner

PROXIMITY BASED AND DATA EXCHANGE AND USER AUTHENTICATION BETWEEN SMART WEARABLE DEVICES

CROSS-REFERENCE TO RELATED APPLICATIONS

This application is a 35 U.S.C. § 111(a) continuation of PCT international application number PCT/US2015/016676 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127116 A1 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices.

2. Discussion

Often, people who are in a relationship want to be more in touch with each other exclusively, and perhaps receive data with respect to each other in relation to their relationship and in general gain a feeling of togetherness. In the past, couples employ external articles to signify their togetherness such as matching clothing, accessories, etc. but these items do not add any additional information to the relationship unless the item is not worn.

Historically, consumer demand exists for users to acquire time-limited extensions to their existing set of devices to enhance or extend their current service or content access. Examples of these could be subscription access to music or TV shows, access to a new level in game, access to new avatar for a limited amount of time or access to new characters in a game. These have traditionally been accomplished via an application purchase, secure DRM for time restriction and remote removal of features after expiry of the rights to that content.

Typically, in order for one device to communicate with another device, the devices must be in a certain range of one another. This is due to things like processing ability and storage. Also, many devices need an authentication of some kind, in order to perform a function of provide a service. Therefore, it is desirable to have a smart wearable device that can automatically sense when a device, such as a non-wearable or media rendering device, is in communication range of the smart wearable device and automatically verify that a particular user has access rights to use a service on that device.

BRIEF SUMMARY

This disclosure describes systems and methods for companion data exchange between smart wearable devices.

One aspect of the present technology is a system and method comprised of two or more wearable where the wearable's are worn by two or more wearer's to monitor and predict the relative intimacy and/or relationship health by tracking the frequency of proximity, heart rate when in proximity with each other and other sensors deriving relaxation, bliss, etc.

The present technology provides two or more wearable where the wearable's are worn by two or more wearer's to monitor and predict the relative intimacy and/or relationship health by tracking the frequency of proximity, heart rate when in proximity with each other and other sensors deriving relaxation, bliss, etc.

Companionship wearable would be worn to monitor and attempt to predict the relative relationship health of a pair of wearers by tracking various aspects of the relationship such as duration of proximity to each other, frequency of proximity, heart rate when in proximity to each other and other sensors deriving relaxation, bliss, etc. It's importance, usefulness and valuableness is only to the two paired wearers.

Another aspect is directed to smart wearable devices and methods for proximity based exchange and authentication.

One aspect of the present technology is a system and method in which a disposable wearable device provides enhanced capabilities to a non-wearable device for a limited period of time by sensing proximity and securely exchanging permissions with the non-wearable device. In one embodiment, the wearable device is capable of sensing one or more bio-signals that are provided to the non-wearable, tactile feedback, or the like. The wearable device may be disposable and may also provide additional tactile feedback for the extended feature (e.g. game feedback, etc).

Another aspect comprises a secure and easy means for service and content providers to provide disposable wearable devices, similar to how a top up card works in the mobile/e commerce world. The systems and methods of the present technology may also aid in securely verifying the person who consumed the product, and because of the disposable nature of the wearable device attached to the body, it can easily be timed out.

This disclosure describes smart wearable devices and methods for authenticating a user's identity and verifying that the user has access to services for use with a non-wearable device, such as a television. In one embodiment, the smart wearable device can authenticate the identity of the user of the smart wearable device using biometrics, such as a user's heart rate signature.

In another embodiment described herein, the smart wearable device can notify the user when the smart wearable device is close to becoming out of range of the non-wearable device.

In yet another embodiment, verification of a user's access rights can be attained by the smart wearable device with a token that indicates current access rights or expiration of access rights. Alternatively, access rights can be provided using additional smart wearable devices that the user could wear. This could be, for example, similar to a charm bracelet, where each device is a "charm" that can grant access rights to different services.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

The present disclosure generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood coritzol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may also include artificial intelligence so that the device can learn and adapt to the wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

Figure 1:
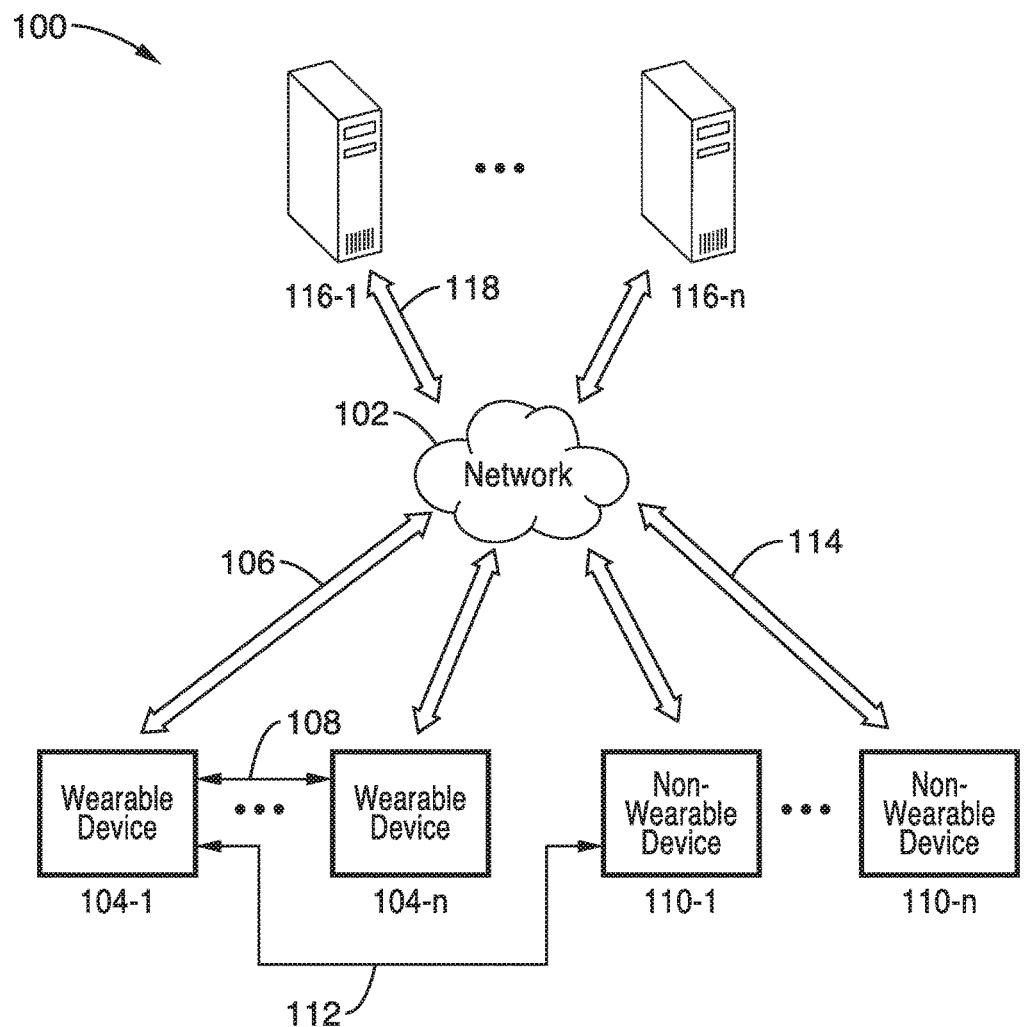
FIG. 1 is a schematic diagram of an embodiment of a smart wearable network described herein.

FIG. 1 illustrates a generalized networked infrastructure (e.g., system) 100 that includes a network 102. The network could, for example, be a local area network or a wide area network such as the Internet. One or more smart wearable devices 104-1 through 104-*n* according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-*n* also may be enabled to communicate with one or more non-wearable devices 110-1 through 110-*n*. The non-wearable devices, which are beyond the scope of this disclosure, may be any conventional "smart" device with a processor, associated operating system, and communications interface. Examples of non-wearable devices include Smartphones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type enabled to communicate with the network 102 through a standard wired or wireless connection 114. In that case, one or more of the smart wearable devices may be enabled to communicate with one or more of the non-wearable devices through the network 102.

One or more servers 116-1 through 116-*n* may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
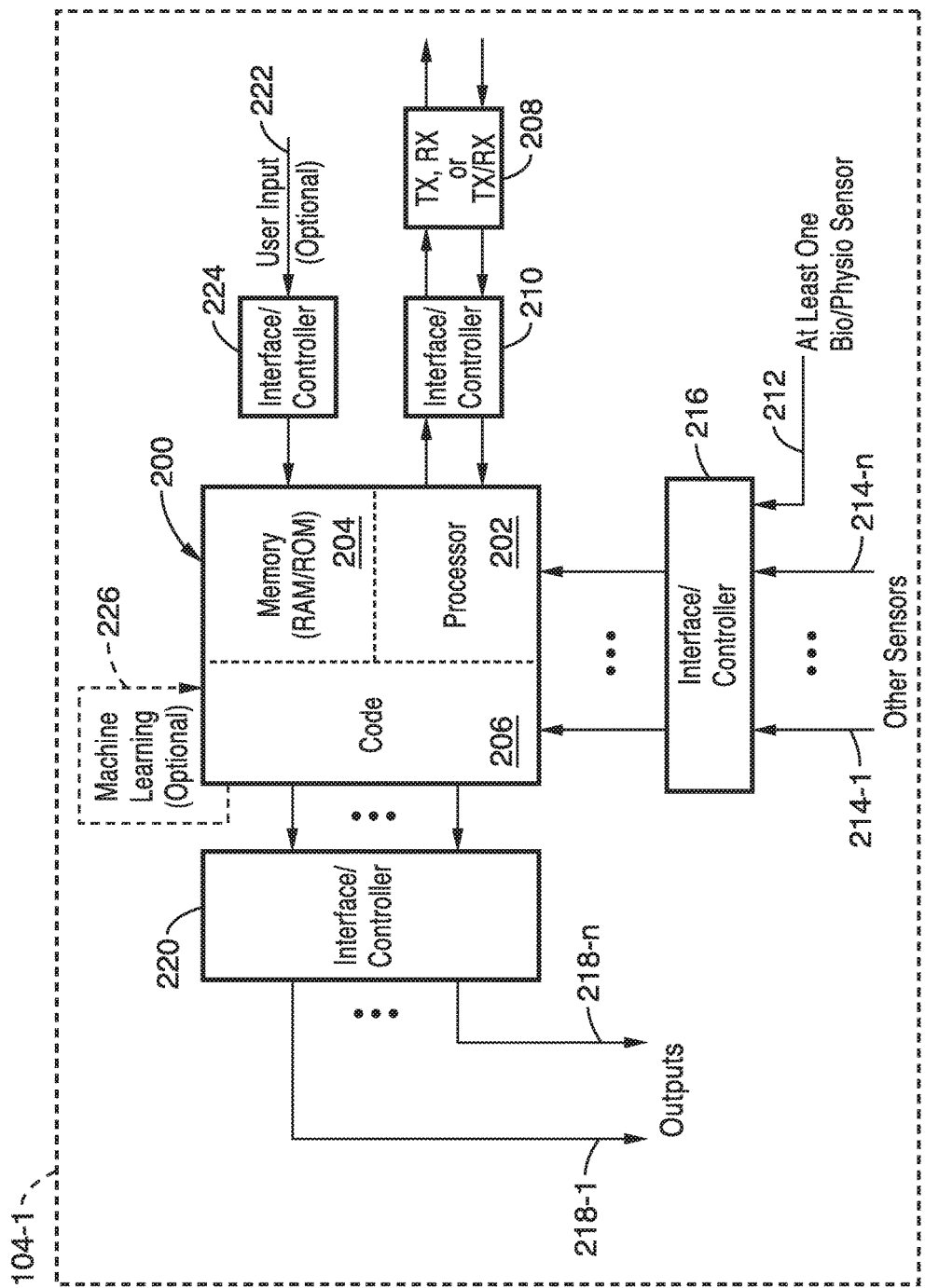
FIG. 2 is a functional block diagram of an embodiment of a smart wearable device as described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-n for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-n to drive one or more output devices (and include those output devices). These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, ankle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Device for Proximity Based Exchange

Figure 3:
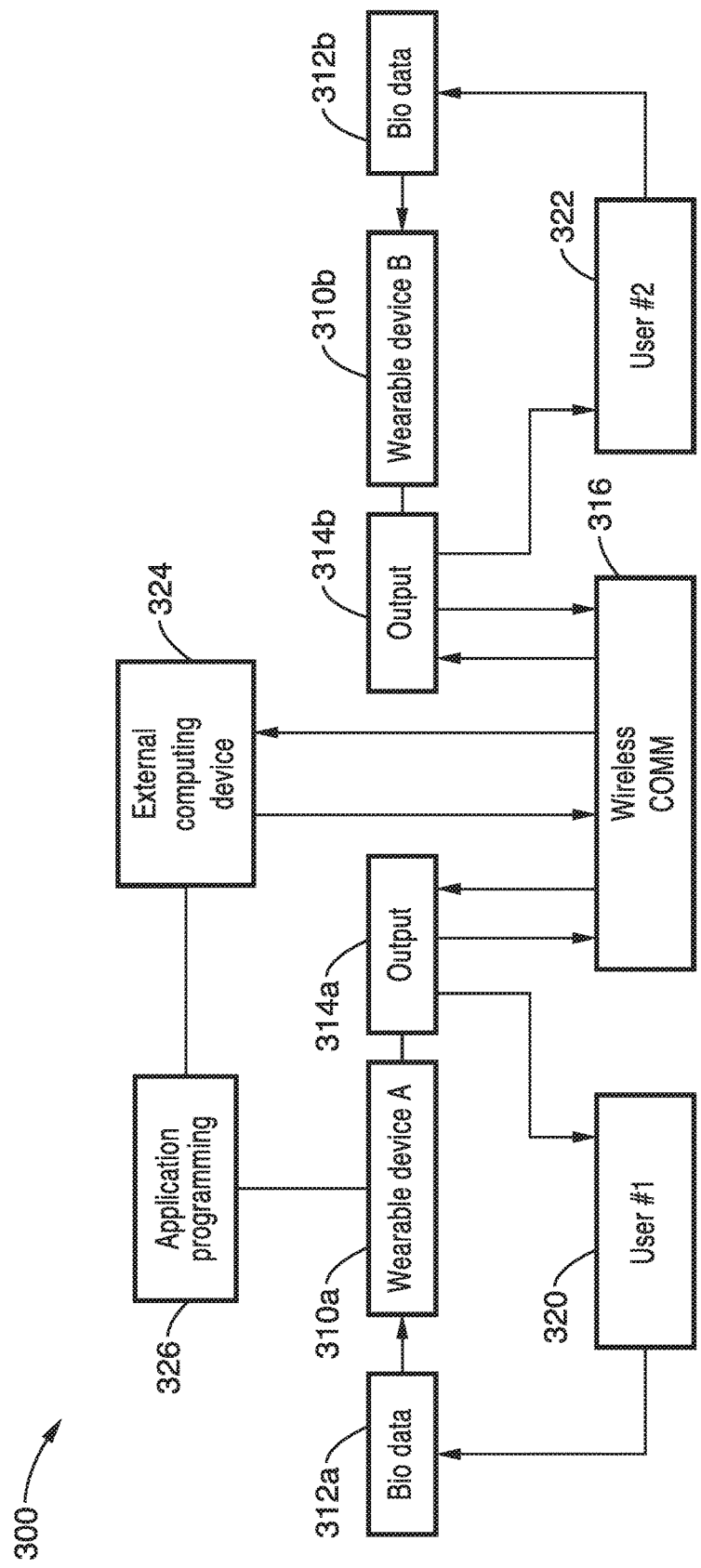
FIG. 3 is a schematic diagram of an embodiment of a smart wearable device and system for companion-based exchange as described herein.

The disclosed devices and methods facilitate companion data exchange between one or more wearable devices and one or more non-wearable devices. Presented in FIG. 3 is a schematic diagram of a system 300 for companion data exchange between a pair of wearable devices 310a and 310b, e.g. in accordance with smart wearable device 104-1 (see FIG. 1 and FIG. 2) and one or more non-wearable devices or external devices 324, e.g. in accordance with non-wearable device 110-1 (see FIG. 1).

Wearable devices 310a and 310b are configured to receive biological/physiological input (e.g. bio data 312a and 312b respectively) from respective users 320 and 322 while the wearable devices are being worn. Such biological/physiological input 342 from the user may comprise data or a signal relating to the user's temperature, pulse, blood pressure, etc. Sensor 350 may also send a probing signal 340 (e.g. a light pulse for oximetry or imaging, etc.) into the user's tissue for retrieval as signal 342.

Wearable devices 310a and 310b are further configured to output data (e.g. data 314a and 314b respectively) to respective users 320 and 322, as well as exchange the data between users 320 and 322 and/or external computing device 324 via wireless communications link 316 (e.g. Wifi, Bluetooth, IR, or other wireless communication means available in the art). Application programming 326 may be installed on one or more of devices 310a and 310b or external computing device 324 (e.g., which may comprise a cell phone, computer, web server, etc.) to facilitate identification of devices, exchange of data, an/or a platform for users to view acquired data.

Figure 4:
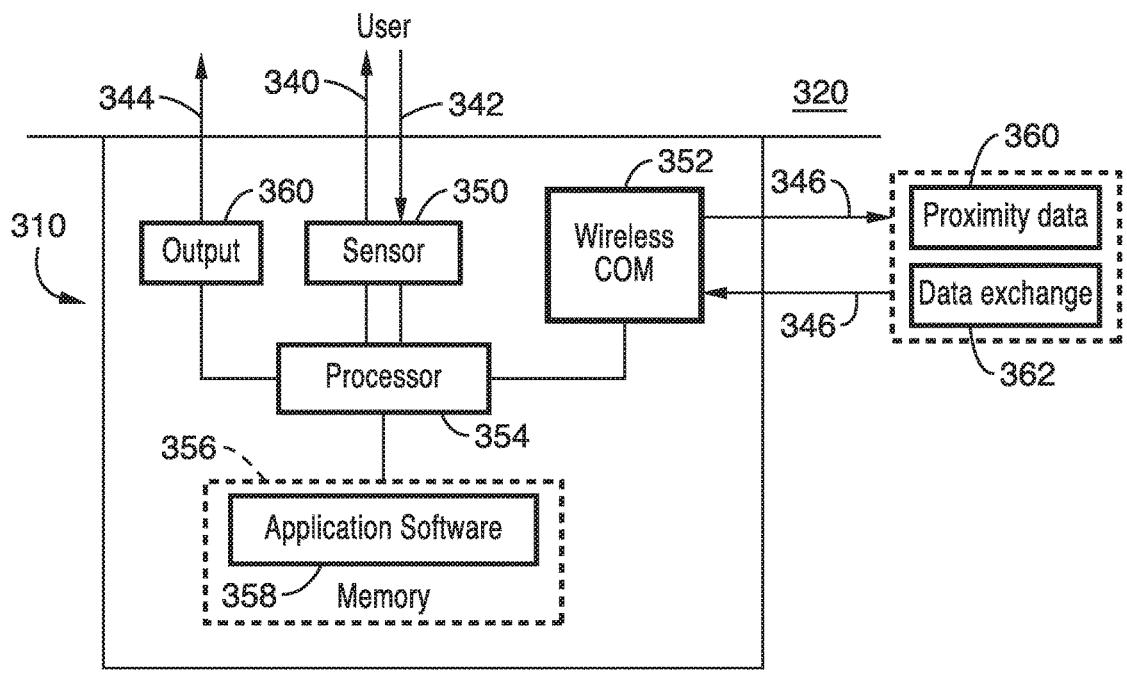
FIG. 4 is a schematic component diagram of an embodiment of a smart wearable device for companion-based exchange in accordance with the present description.

Referring to the component diagram of FIG. 4, wearable device 310 may comprise a number of components for acquiring/exchanging information, such as an environmental sensor 350 configured for sending a signal 340 into or receiving a signal/data/measurements from user 320 for the purposes of measuring one or more biological/physiological conditions of the user, e.g. temperature, heart rate, movement, etc.

The wearable device may further comprise memory 356 for storing programming application programming 358 (see also code 206 of FIG. 2), processor 354 for executing the programming 358, and wireless communications interface/circuitry 352 for detection and/or data transfer with other wearable and/or non-wearable devices (e.g. via a wireless link 346 such as Wifi, Bluetooth, IR, etc.). As will be explained in further detail below, the corn link 346 of device 310 may wirelessly communicate proximity data 360 relating to the location of the device 310 (and accordingly the wearing user, i.e. user 320) in proximity with other devices (e.g. device 310b and its wearing user, i.e. user 322). The corn link 346 of device 310 may also wirelessly communicate exchange data 362 between devices 310a and 310b, the exchange data preferably comprising environmental/biometric data 342 from sensor 350.

Device 310 may also comprise an output 360 for outputting sensory or visual data 344 to the user, such as a vibration, warming sensation, sound (e.g. via a speaker), or a visible indication such as an illumination or the like. Visual illumination may be via an LED or an actual display, or other output device known in the art. Other circuitry, such as that shown in device 104 of FIG. 2, may also be incorporated, as appropriate for the specific device functionality.

Wearable devices 310*a* and 310*b* may be worn by respective wearers 320 and 322 not whether or not in each other's presence. When the wearers 320 and 322 come within proximity of each other while wearing devices 310*a*, 310*b*, the wearable devices 310*a* and 310*b* may identify each other's presence (e.g. via Bluetooth or Wifi or even NFC by touch through wireless corn 352), record such occurrence in memory, and/or give feedback to either or both of the wearers 320, 322 (e.g. a subtle or soothing vibration, slight increase in temperature, special ringtone, etc.). The wearable devices 310*a*, 310*b* ideally will be gathering one or more biometric datasets from the wearer that can be relayed to the other wearer. For example, heart rate may be measured by the heart rate bio sensor 350 in the wearable device 310 itself, but the wearable device 310 doesn't necessarily have to process the heart rate data. Duration of how long the wearers 320 and 322 are in relative range of each other may also be tracked, and tallied for later retrieval. Such data may be recalled by the wearable device itself, or accessed via external device 324 through an interface provided by application programming 326. For example, either of the users may track the total number of hours that the two users 320, 322 are in close proximity to each other for a given period of time, e.g. daily, monthly or yearly totals or frequency.

While the wearers are not in proximity of each other, application programming 326 or 356 may be configured to track and compile other forms of connection with the other user or users, or other forms of communication, such as frequency of phone calls, duration of phone calls, number of SMS/MMS and other forms of communication in social media spheres (posts to Facebook, likes on Instagram, etc.)

When one or both of the wearers 320, 322 are not wearing their wearable device 310, this could be a sign of a relationship that potentially is becoming unhealthy and the other wearable device (worn by the secondary wearer) could be notified that the first wearer is no longer wearing their wearable. Such activities may also be tracked for later collection.

The health of a relationship between wearers 320, 322 may also be rated and directed back to the wearers 320, 322 or their wearable devices 310*a*, 310*b* in some fashion.

In a further example, the application software 358 may be configured to target a couple who recently started dating. Here, for the purpose of the explanation, it is assumed that the user 320 and the user 322 are dating. The wearable device 320 and the wearable device 322 can be registered respectively to the user 320's and the user 322's network service account (e.g., social media account), and then the devices 310*a* and 310*b* can be paired up. Network services can be implemented on all or a part of the servers 116-1 to 116-10. Network services may provide each user with an option to register his/her wearable device and may have an API via which the registered wearable device can communicate with the network services by exchanging information including sensor information such as data or a signal relating to the user's temperature, pulse, blood pressure, etc. Also the registered wearable device, depending on a setting of the account at the user's account, may automatically sent the total number of hours that the two users 320, 322 are in close proximity to each other for a given period of time, e.g. daily, monthly or yearly totals or frequency.

Then, the network service may allow only the user 320 and the user 322 can see the information of the total number of hours that the two users 320, 322 are in close proximity to each other for a given period of time. By that, users 320 and 322 may be able to feel that their personal information is secured. Depending on the length of the total number of hours, the network service may let the wearable devices 310*a* and 310*b* to output a special signal, such as special lighting pattern of LED or special images shown on the display, with or without sound.

For example, the special signal can be made when the length of the total number of hours exceeds a predetermined threshold (e.g., 10 hours per week). There may be different special signals (e.g., different lighting pattern of LED, different images shown on the display, different sound pattern) to be outputted, depending on the length from the time the users 320 and 322 started dating. The time of start of their dating may be registered to the network account. The special signal is not limited to the examples above. For example, it may be that a special item on both of the network services account of users 320 and 322 comes up when some conditions are met (e.g., the total number of hours exceeds a predetermined threshold).

The above is explained as the network services play a main role managing the information of the users 320 and 322. It may be a different configuration. For example, all or a part of the sensor information (or processed information from sensor information such as the total number of hours that the two users 320, 322 are in close proximity to each other for a given period of time) can be stored in devices 310*a* and 310*b*.

Figure 5:
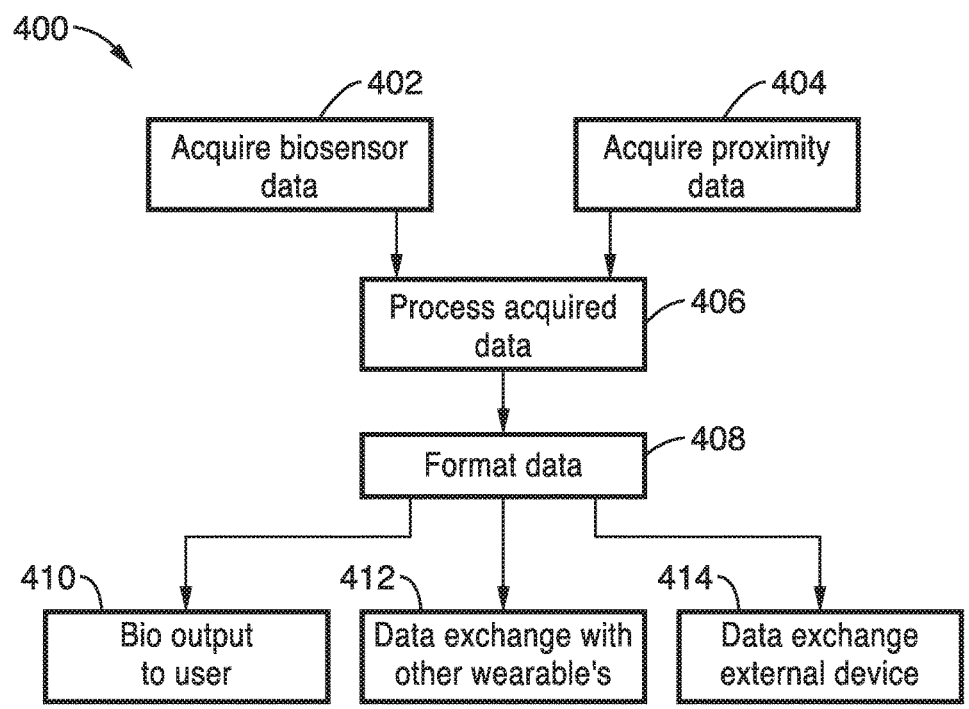
FIG. 5 is a flow diagram of a method for companion-based exchange using a wearable device as described herein.

FIG. 5 shows a flow diagram of an exemplary method 400 for companion-based exchange between wearable devices in accordance with the present disclosure. It is appreciated that method 400 may be employed as an algorithm or software routine as part of code 206 in FIG. 2. At block 402, the wearable device 310 is programmed to obtain biosensor data 342 via sensor 350 at specified times/intervals via wireless comm. 352. If another wearable device belonging to a wearer of interest is in proximity the device 310 may acquire proximity data 360 at step 404. Data acquisition steps 402 and 404 may be acquired simultaneously or in series. The data from steps 402 and/or 404 is then processed via application software 356, and then formatted at step 408 according to one or more of three outputs: 1) bio-output 410 to the user 320 via output device 360 (e.g. vibration, warming, light or sound emission, or visual display), 2) data exchange 412 with other users (e.g. with wearable devices) via wireless com 352; and 3) data exchange 414 to an external device 324.

C. Smart Wearable Device for Proximity Based Exchange

Figure 6:
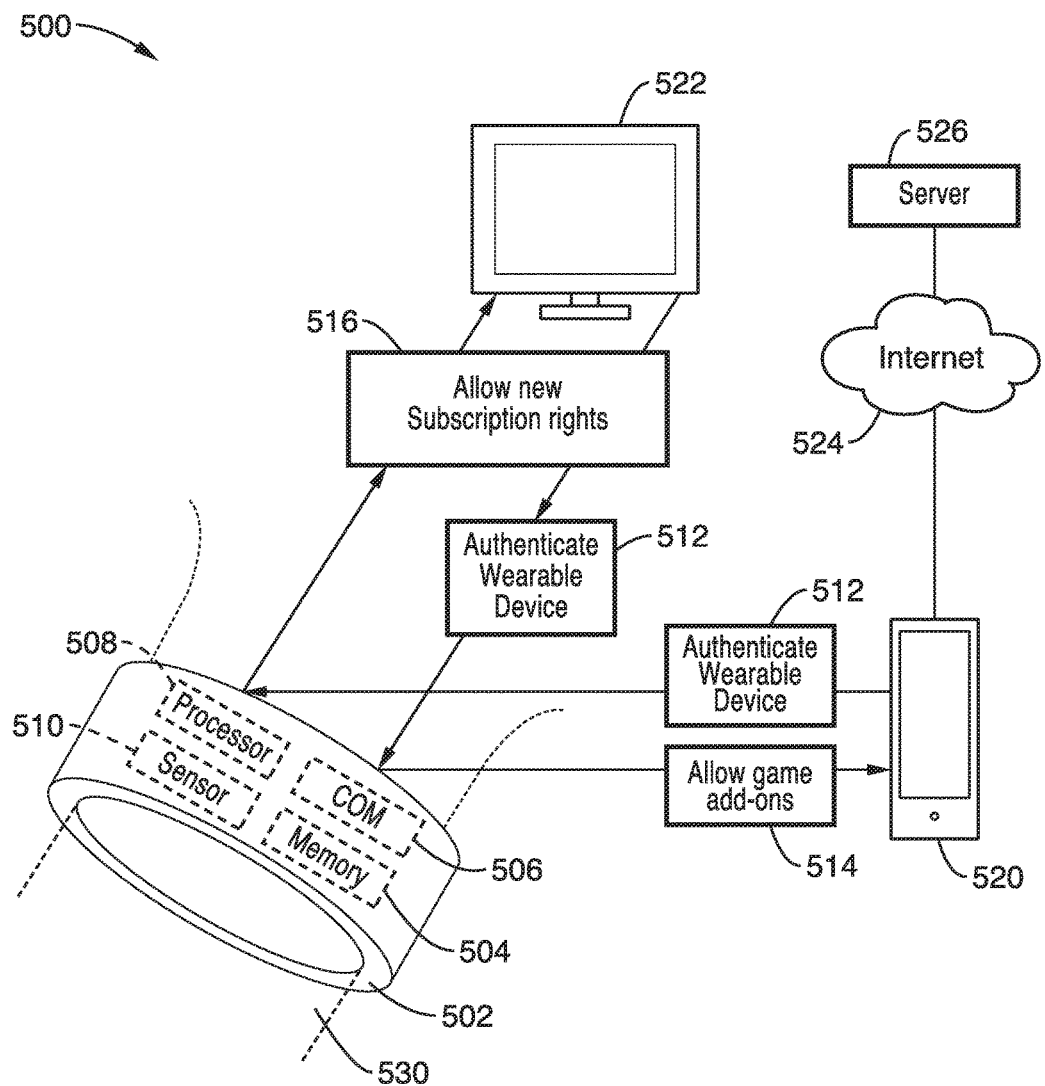
FIG. 6 is a schematic diagram of an embodiment of a smart wearable device and system for proximity-based exchange described herein.

The disclosed devices and methods facilitate the acquisition of proximity based exchange between one or more wearable devices and one or more non-wearable devices. Presented in FIG. 6 is a schematic diagram of a system 500 for proximity based exchange between a wearable device 502, e.g. in accordance with smart wearable device 104-1 (see FIG. 1 and FIG. 2) and one or more non-wearable devices 520, 522, e.g. in accordance with non-wearable device 110-1 (see FIG. 1).

In a preferred embodiment, a user may purchase (e.g. from a store or other retail outlet) a wearable device 502 pre-programmed with specific capabilities. Device 502 is shown in the form of a wrist band 502 for placement over a person's wrist. It is appreciated that the form factor, casing/housing, etc. of the wearable device 502 may comprise any number of forms, e.g. adhesive based product such as a sticker or band-aid, garment, glove, helmet, etc.

Wearable device 502 may comprise a number of components such as an environmental sensor 510 configured for measuring one or more biological/physiological conditions of the user, e.g. temperature, heart rate, movement, etc., along with memory 504 for storing programming (e.g. code 206), processor 508 for executing the programming, and communications interface/circuitry 506 for communicating with other wearable and/or non-wearable devices (e.g. via Wifi, Bluetooth, IR, etc.). Other circuitry, such as that shown in device 104 of FIG. 2, may also be incorporated, as appropriate for the specific device functionality.

In another embodiment (not shown), one or more of the above components may be in form of an RFID chip that may be activated by a scanner at point of purchase (e.g. permission are activated upon scanning at purchase).

Figure 7:
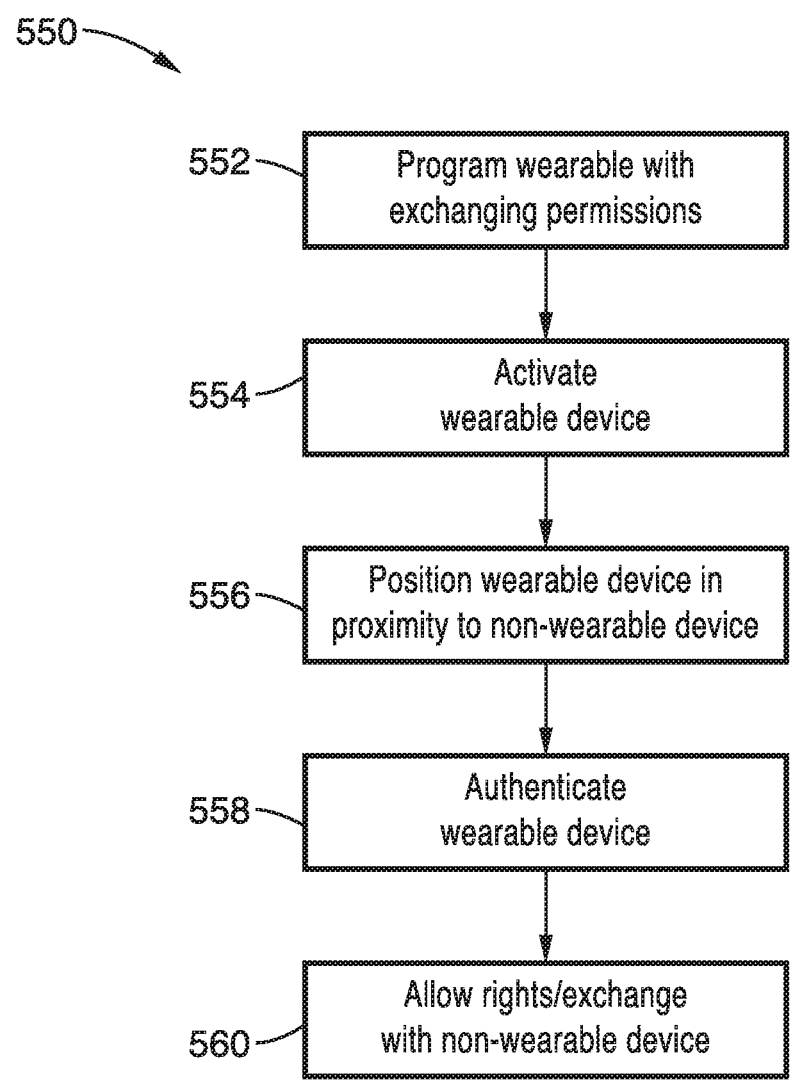
FIG. 7 is a flow diagram of method for proximity-based exchange using a wearable device described herein.

FIG. 7 shows a flow diagram of an exemplary method 550 for proximity based exchange with a wearable device in accordance with the present disclosure. It is appreciated that method 550 may be employed as an algorithm or software routine as part of code 206 in FIG. 2. At block 552, the wearable device 502 is programmed with exchange permissions. The exchange permissions may be to a number of different devices or applications depending on the product, as will be described in further detail below. Activation of the permissions (block 554) may be performed at this time, or at a later specified time (e.g. point of purchase).

At block 556, when the user wears the wearable device 502 on a specified location on the body in proximity of a non-wearable device (e.g. smart phone 520 or web enabled computer/DVR/TV 522) a secure exchange of data/information is performed to authenticate (block 512 FIG. 6 and block 558 of FIG. 7) the wearable device 502 and ensure the rights exchanged with the wearable device 502. At block 560, the wearable device may then get updated data associated with an extended capability, new features or like exchange of information. Such feature may comprise, but are not limited to, new subscription rights 516 or game ad-ons 514 as shown in FIG. 6. Examples of these could be subscription access to music or TV shows, access to a new level in game, access to new avatar for a limited amount of time or access to new characters in a game. The permissions and/or data exchanged may be stored in memory 504.

In one embodiment, authentication step 558 and/or rights/exchange step 560 may include further synchronization and/or coupling to data server 526 over internet connection 524. Server 526 may comprise permissions/subscription data, etc., in addition to data relating to valid purchase of the wearable product (e.g. the wearable device 502 may have an associated bar code that is scanned at point of purchase for validating the purchase).

In a preferred embodiment, the wearable device is configured to be disposable. Because of the inherent nature of the disposable wearable device, the rights would be terminated as the wearable is disposed and hence it prevents possible misuse. For example, the bio-sensor 510 may be configured to sense the specific user, or allow one-time use so that once the user takes off the wearable device 502, the exchange rights terminate. More specifically, the sensor may read a fingerprint, body temperature, retina, or other indicator of the user that would prohibit use from another user.

One exemplary use of the wearable device would be purchase by a user of a disposable band-aid like wearable (e.g. with Disney or other associated indicia), and then when sticks/adheres it to his/her body in proximity to non-wearable device 520/522 is granted a new character in a game, access to wallpaper, ringtones etc.

In case of content exchange at step 560, in one exemplary configuration the wearable device 502 may be in the form of a subscription content management device such as a music (e.g. mp3 or other streamable format) subscription in the form of a wearable sticker or a video content subscription sticker device, and as long as the user wears the device and is in proximity of a TV 522, smart phone 520, or other non-wearable device capable of download and/or streaming, the will have rights to enjoy the predetermined content for the term specified.

D. Smart Wearable Device for User Authentication, Access Rights Verification and Range Notification.

Figure 8:
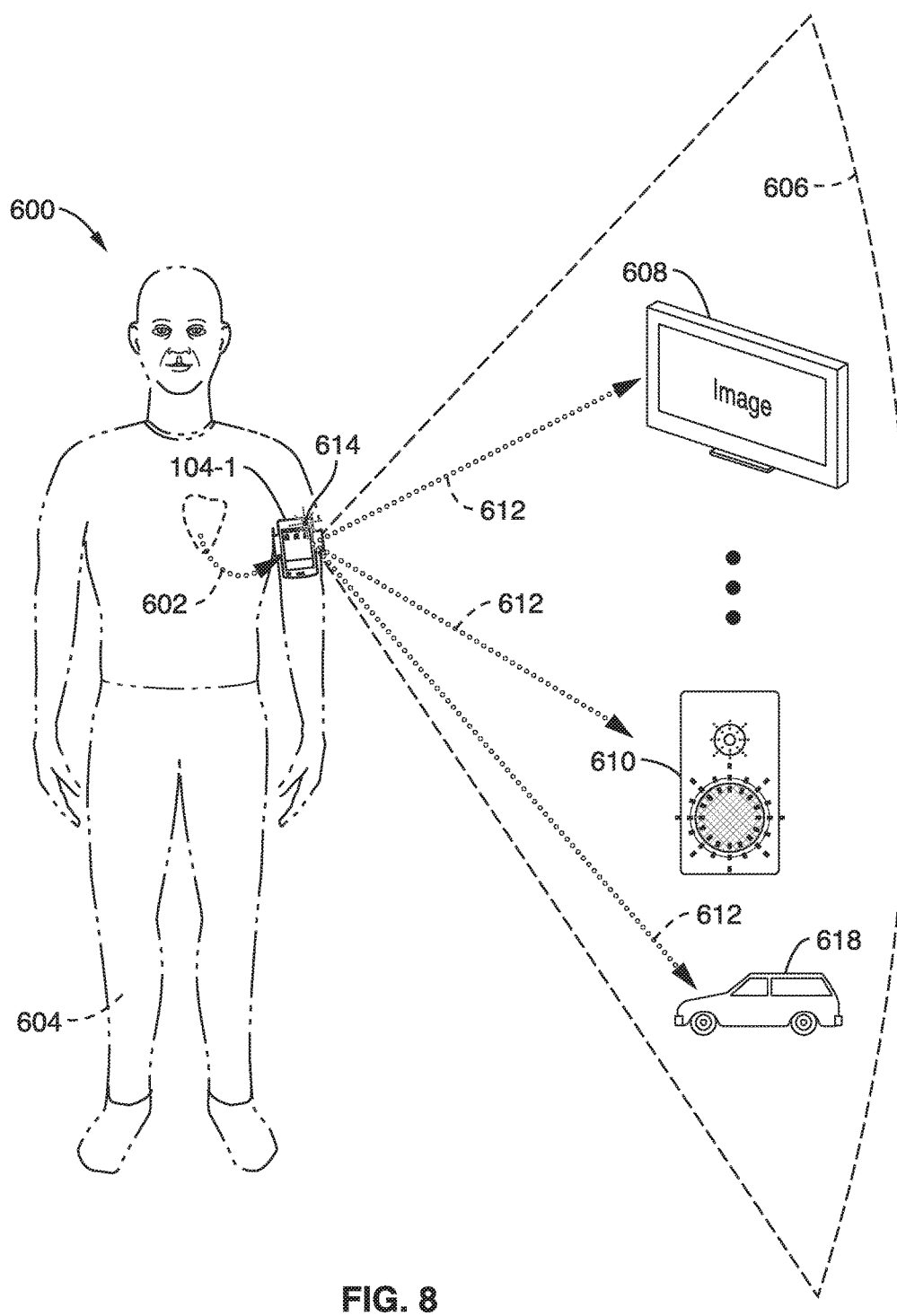
FIG. 8 is a schematic diagram showing a smart wearable device authenticating a user to access services for use with other devices within range of the smart wearable device, and providing notification to the user, according to an embodiment of the disclosure.

Referring now to FIG. 8, a schematic diagram 600 is shown where one embodiment of a smart wearable device 104-1 may detect within a certain range 606, non-wearable devices 608, 610, 618 that can be utilized by the smart wearable device upon communication between devices. This may be accomplished by the smart wearable device pinging the non-wearable devices or determining Bluetooth or GPS signal strength or even Wi-FI positioning.

Typically, in order for a user to gain access to certain services, such as subscription based services, their identity must first be authenticated and access rights must be determined. In the embodiment shown in FIG. 8, the smart wearable device may authenticate 602 the identity of a user 604 by way of biometrics. Specifically, the identity of the user 604 in this exemplary system is established by authenticating 602 the user's heart rate signature.

After the user's identity has been authenticated 602, the smart wearable device may also verify that the user has access rights to services, which may be used in conjunction with the detected non-wearable devices 608, 610, 618 that are within a certain range 606. The authentication mechanism to enable access to services on the non-wearable device, or renderer, may be a wearable token indicating current access rights or expiration. For instance, a user may have access to media services, or a user may have access to special offers or coupons, or a user may have access to special powers for their gaming character that can only be used by that user and only when within a certain range of a non-wearable device. The token may be contained within the smart wearable device (semantic web based (SWB), for example), or the token may be in the form of a collection of smart wearable devices themselves, or may be collected, like charms on a bracelet. If the access rights to the service are verified, the smart wearable device may grant access 612 to the service for use on the detected non-wearable devices 608, 610 within range 606.

The smart wearable device may also notify the user when they have been authorized to access the service or when the smart wearable device is getting close to the out of range distance from the non-wearable device the service is being used with. For instance, if a user is watching a movie on a television made available by the smart wearable device and begins to move too far away from the television for the smart wearable device and the television to communicate, the smart wearable device 104-1 may light up 614 (or change color or sound an alarm, etc.) to notify the user. This can be important for providing uninterrupted service because the boundary limitations between the smart wearable device and non-wearable device are not visible and can be different depending on the communication interface being used, services being accessed, etc.

With the wearable device 614 worn by the user in another embodiment, the user can also turn on a car 618 (e.g., the engine if the car is a regular car or a hybrid car, the motor if the car is an electric car or a hybrid car). The condition of turning on the car 618 is preferably a function of whether the user is identified by the wearable device 614 and the wearable device 614 is within a certain range of the car.

Figure 9:
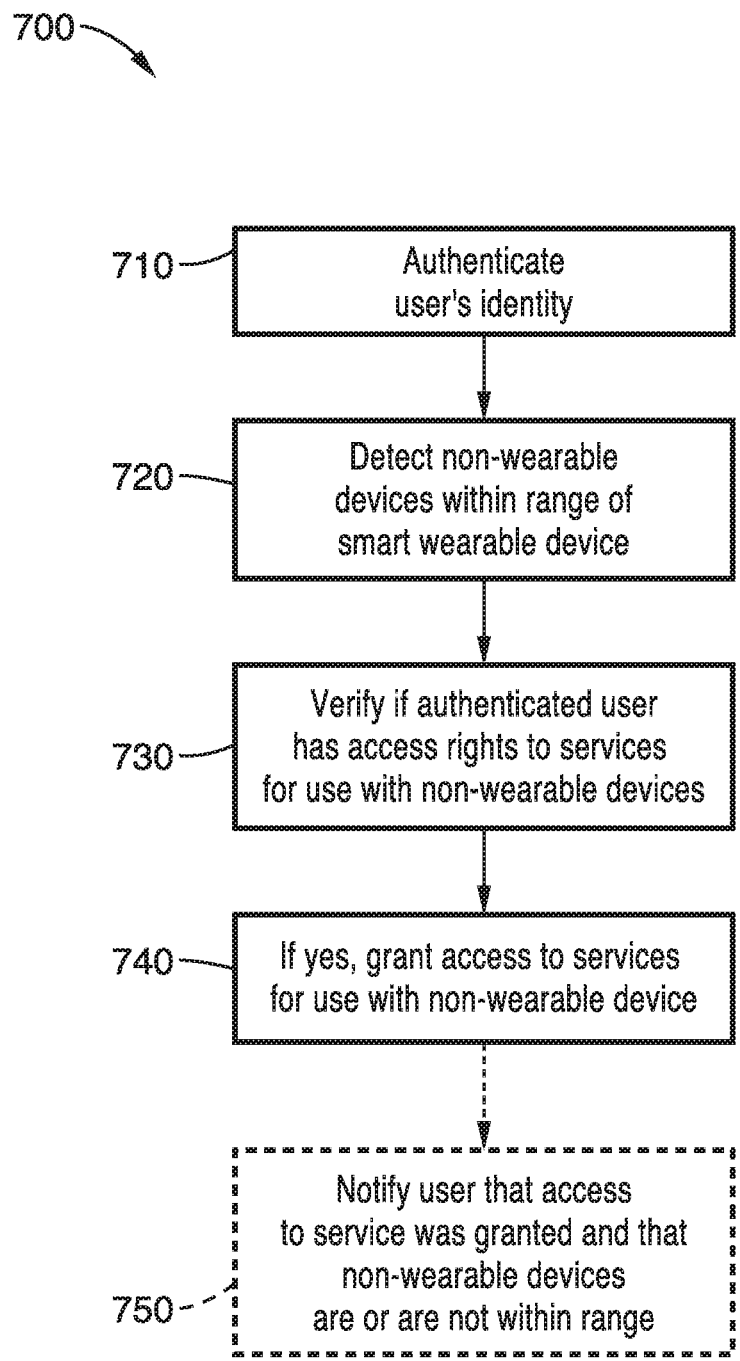
FIG. 9 is a flow diagram of an exemplary method of a smart wearable device authenticating a user to access services for use with other devices within range of the wearable device and providing notification to the user.

Referring now to FIG. 9, a flow diagram 700 is shown of an exemplary method for authenticating the identity of a user and verifying access rights to services for use with non-wearable devices within communication range of the smart wearable device. In this embodiment example, the smart wearable device may authenticate the user's identity by way of biometrics or other authentication mechanism 710. The smart wearable device may then detect non-wearable devices that are within range of the smart wearable device 720. These non-wearable devices may be media or other rendering device that can be used in conjunction with services in which the user has access. Such devices include, but are not limited to, smart televisions, tablet computers, smart monitors, etc. If the user has purchased a service, such as a subscription based service streaming media, the smart wearable device may verify that the authenticated user has access rights to the service for use with the detected non-wearable devices 730. If verification is a success, the smart wearable device may grant access to the service and the service may be used on the detected non-wearable device within communications range of the smart wearable device 740. Optionally, the smart wearable device may provide notification using one or more output devices or forms when the smart wearable device has granted access to the user's service and when there are non-wearable devices within range of the smart wearable device 750. This notification may also take place when the smart wearable device begins to move out of range of the non-wearable device. This notification feature can be useful when the user begins to move the smart wearable device out of range of the non-wearable device, because the service connection can be lost if the devices are unable to communicate as a result of being too far away from one another.

With respect to the flow diagram 700 of FIG. 9, first, the user is authenticated by the wearable device. This authentication may be done by the user's biometric data or some other information. The example of some other information is a particular pattern of shaking the wearable device. When the wearable device is a wrist type band, a pattern of shaking the user's wrist (i.e., shaking the wearable device) may be sensed by the sensor implemented on the wearable device. For example, quick twist of the wrist band type wearable device three times within two second may be registered on the memory 204 of the wearable device. In that example, the wearable device may have an authentication mode during which the wearable device can accept the authentication. The wearable device may keep assuming that the same user is using that wearable device until the time the wearable device senses the motion that the user is removing the worn wearable device. The wearable device may sense such a motion by sensing the unbuckling motion of the wrist band of the wearable device when the wearable device is a wrist type. One example of sensing such a motion is that the wearable device may pre-store the typical patterns of the sensor information when detecting the unbuckling motion of the wrist band of the wearable device and then compare the information regarding such typical patterns with the sensed data when the wearable device is authentication mode.

When the user gets close to the car 618 (i.e. gets in the certain range of the car 618), and the user is authenticated by the wearable device 614, the wearable device 614 may unlock the door of the car, or perform other functions (e.g. AC, etc.). Further, when the user is in the car 618, the car 618 may recognize that the user is in the car by detecting the signal from the wearable device, such as Bluetooth, NFC. The engine or the motor of the car may be turned on when the wearable device 614 is in the proximity of the steering wheel (not shown). In this case, the steering wheel and the wearable device may have some short range wireless communication interface circuit (not shown) such as NFC transceiver to decide that the wearable device is in the proximity of the steering wheel. In this example, the user may be able to turn on the engine or the motor when the user hold the steering wheel with hands on which the wearable device is worn. The car may keep the car's engine or the motor on unless the user pushes some special button on the car (e.g., OFF button, not shown). By that, it can be avoided that the user inadvertently turns off the car's engine or the motor by releasing his hand from the steering wheel.

In step 750, the wearable device 614 may notify the user by a unique pattern of the vibration when the user gets out of the car.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A wearable device, the device comprising: (a) a housing; (b) one or more sensors coupled to the housing, wherein at least one of the one or more sensors is configured for sensing biological or physiological input; (c) one or more communications interfaces; (d) a processor; and (e) programming stored in a non-transitory medium, wherein the programming is readable and executable by the processor, and wherein the programming performs steps comprising: (i) sensing biological or physiological input of a first user via the one or more sensors; (ii) identifying a second wearable device worn by a second user in proximity to the wearable device; and (iii) exchanging data with the second wearable device via the one or more communication interfaces.

2. A wearable device as in any of the previous embodiments, wherein the data comprises data relating to the biological or physiological input of the first user.

3. A wearable device as in any of the previous embodiments, wherein the data comprises data relating to the biological or physiological input of the second user.

4. A wearable device as in any of the previous embodiments, wherein the data comprises data relating to the proximity of the first user with the second user.

5. A wearable device as in any of the previous embodiments, wherein the proximity data is stored for collection from the first or second users.

6. A wearable device as in any of the previous embodiments, the programming further configured for: ending an output signal to the first user of the second user's proximity to the first user; said output signal being one or more of: a vibration, an audible sound, or visible emission.

7. A wearable device as in any of the previous embodiments, wherein the biological or physiological input comprises a signal relating to one or more of the first user's: heartbeat, temperature, or blood pressure.

8. A system for communicating between a first user and a second user, comprising: (A) a first wearable device and a second wearable device, each of the first and second wearable devices comprising: (i) a housing; (ii) one or more sensors coupled to the housing, wherein at least one of the one or more sensors is configured for sensing biological or physiological input; (iii) one or more communications interfaces; (iv) a processor; and (v) programming stored in a non-transitory medium, wherein the programming is readable and executable by the processor, and wherein the programming performs steps comprising: (a) sensing biological or physiological input of a first user via the one or more sensors on the first wearable device; (b) identifying a second wearable device worn by a second user in proximity to the first wearable device; and (c) exchanging data between the first wearable device and the second wearable device.

9. A system as in any of the previous embodiments, wherein the data comprises data relating to the biological or physiological input of the first user.

10. A system as in any of the previous embodiments, wherein the data comprises data relating to the biological or physiological input of the second user.

11. A system as in any of the previous embodiments, wherein the data comprises data relating to the proximity of the first user with the second user.

12. A system as in any of the previous embodiments, wherein the proximity data is stored for collection for the first or second users.

13. A system as in any of the previous embodiments, the programming further configured for: sending an output signal from the first wearable device to the first user of the second user's proximity to the first user; said output signal being one or more of: a vibration, an audible sound, or visible emission.

14. A system as in any of the previous embodiments, wherein the biological or physiological input comprises a signal relating to one or more of the first user's: heartbeat, temperature, or blood pressure.

15. A method for communicating between a first user wearing a first wearable device and a second user using a second wearable device, comprising: sensing biological or physiological input of a first user via one or more sensors coupled to the first wearable device; identifying a second wearable device worn by a second user in proximity to the wearable device; and exchanging data with the second wearable device via one or more communication interfaces on the first wearable device.

16. A method as in any of the previous embodiments, wherein the data comprises data relating to the biological or physiological input of the first user or the second user.

17. A method as in any of the previous embodiments wherein the data comprises data relating to the proximity of the first user with the second user.

18. A method as in any of the previous embodiments wherein the proximity data is stored for collection from the first or second users.

19. A method as in any of the previous embodiments, further comprising: sending an output signal to the first user of the second user's proximity to the first user; said output signal being one or more of: a vibration, an audible sound, or visible emission.

20. A method as in any of the previous embodiments, wherein the biological or physiological input comprises a signal relating to one or more of the first user's: heartbeat, temperature, or blood pressure.

21. A wearable device, the device comprising: (a) a housing, wherein the housing encases components of a wearable device; (b) one or more sensors, wherein at least one sensor is configured for sensing biological or physiological input; (c) one or more communications interfaces; (d) a processor; and (e) programming stored in a non-transitory medium, wherein the programming is readable and executable by the processor, and wherein the programming performs steps comprising: (i) sensing one or more devices in proximity to the wearable device; (ii) communicating with the one or more devices; and (iii) acquiring one or more permissions relating to data associated with the wearable device or the one or more devices.

22. A wearable device as in any of the previous embodiments, wherein the data comprises application programming associated with the one or more devices.

23. A wearable device as in any of the previous embodiments, the programming further configured for downloading the application programming from a remote server to the one or more devices.

24. A wearable device as in any of the previous embodiments, wherein the application programming comprises a subscription service.

25. A wearable device as in any of the previous embodiments, wherein the application programming comprises a game software or a component thereof.

26. A wearable device as in any of the previous embodiments, further comprising: one or more environmental sensors coupled to the processor; wherein the one or more environmental sensors are configured to sense a physiological or biological characteristic associated with a user of the wearable device.

27. A wearable device as in any of the previous embodiments, wherein acquiring one or more permissions is a function of the one or more environmental sensors sensing a predetermined physiological or biological characteristic of the user.

28. A wearable device, the device comprising: (a) a housing, wherein the housing encases components of a wearable smart device; (b) one or more sensors, wherein at least one sensor is configured for sensing biological or physiological input; (c) one or more communications interfaces; (d) a processor; and (e) programming stored in a non-transitory medium, wherein the programming is readable and executable by the processor, and wherein the programming performs steps comprising: (i) sensing one or more devices in proximity to the wearable device; (ii) communicating with the one or more devices; and (iii) acquiring the data associated with the wearable device or the one or more devices.

29. A wearable device as in any of the previous embodiments, wherein acquiring data comprises acquiring one or more permissions relating to data associated with the wearable device or the one or more devices 30. A wearable device as in any of the previous embodiments, wherein the data comprises application programming associated with the one or more devices.

31. A wearable device as in any of the previous embodiments, the programming further configured for downloading the programming from a remote server to the one or more devices.

32. A wearable device as in any of the previous embodiments, wherein the application programming comprises a subscription service.

33. A wearable device as in any of the previous embodiments, wherein the application programming comprises a game software or a component thereof.

34. A wearable device as in any of the previous embodiments, further comprising: one or more environmental sensors coupled to the processor; wherein the one or more environmental sensors are configured to sense a physiological or biological characteristic associated with a user of the wearable device.

35. A wearable device as in any of the previous embodiments, wherein the acquiring one or more permissions is a function of the one or more environmental sensors sensing a predetermined physiological or biological characteristic of the user.

36. A system for proximity-based exchange between a wearable device and a non-wearable device, comprising: (a) a processor; and (b) programming stored in a non-transitory medium, wherein the programming is readable and executable by the processor, and wherein the programming performs steps comprising: (i) sensing a non-wearable device in proximity to the wearable device; (ii) communicating between the non-wearable device and wearable device; and (iii) acquiring one or more permissions relating to data associated with the wearable device or non-wearable device.

37. A system as in any of the previous embodiments, wherein the data comprises application programming associated with the one or more devices; and wherein the programming is further configured for downloading the programming from a remote server to the one or more devices.

38. A system as in any of the previous embodiments, wherein the programming comprises a subscription service, game software, or a component thereof.

39. A system as in any of the previous embodiments, further comprising: one or more environmental sensors coupled to the processor; wherein the one or more environmental sensors are configured to sense a physiological or biological characteristic associated with a user of the wearable device.

40. A system as in any of the previous embodiments, wherein the acquiring one or more permissions is a function of the one or more environmental sensors sensing a predetermined physiological or biological characteristic of the user.

41. A smart wearable device, the device comprising: (a) a housing, wherein the housing encases components of a wearable smart device; (b) one or more sensors, wherein at least one sensor is a biological sensor configured to acquire biological input; (c) one or more output devices; (d) a memory; (e) one or more communications interfaces; (f) a processor; and (g) programming residing in a non-transitory computer readable medium, wherein the programming is executable by the computer processor and configured to: (i) authenticate a user's identity; (ii) detect a non-wearable device that is in range of the smart wearable device's one or more communications interfaces; (iii) verify the authenticated user has access rights to services for use with the non-wearable device; and (iv) if access rights are verified, grant access to the services.

42. The device of any preceding embodiment, wherein said programming is further configured to: notify the authenticated user when their access rights to services have been verified, wherein notification occurs through the output device on the smart wearable device.

43. The device of any preceding embodiment, wherein said programming is further configured to: notify the user when the smart wearable device is out of range for communicating with the non-wearable device, wherein notification occurs through the output device on the smart wearable device.

44. The device of any preceding embodiment, wherein a user's identity is authenticated using biometrics.

45. The device of any preceding embodiment, wherein the one or more communications interfaces are selected from the group consisting of a wired communications interface, a wireless communications interface, a cellular communications interface, a WiFi communications interface, a near field communications interface, an infrared communications interface, ZigBee communications interface, a Z-Wave communications interface and a Bluetooth communications interface.

46. The device of any preceding embodiment, wherein access rights to services are provided to the user in the form of a token within the smart wearable device, wherein the token indicates current access rights or expiration of access rights.

47. The device of any preceding embodiment, wherein access rights to services are provided to the user in the form of multiple smart wearable devices.

48. The device of any preceding embodiment, wherein the smart wearable device has a platform selected from the group consisting of hand worn devices, finger worn devices, wrist worn devices, head worn devices, arm worn devices, leg worn devices, ankle worn devices, foot worn devices, toe worn devices, watches, eyeglasses, rings, bracelets, necklaces, articles of jewelry, articles of clothing, shoes, hats, contact lenses, and gloves.

49. A computer implemented method for a smart wearable device user authentication and non-wearable device range notification, the method comprising: (a) providing a smart wearable device, the device comprising: (i) a housing, wherein the housing encases components of a wearable smart device; (ii) one or more sensors, wherein at least one sensor is a biological sensor configured to acquire biological input; (iii) one or more output devices; (iv) a memory; (v) one or more communications interfaces; and (vi) a processor; (b) authenticating a user's identity; (c) detecting a non-wearable device that is in range of the smart wearable device's one or more communications interfaces; (d) verifying the authenticated user has access rights to services for use with the non-wearable device; and (e) if access rights are verified, granting access to the services; (f) wherein said method is performed by executing programming on at least one computer processor, said programming residing on a non-transitory medium readable by the computer processor.

50. The method of any preceding embodiment, further comprising: notifying the user when the smart wearable device is out of range for communicating with the non-wearable device, wherein notification occurs through the output device on the smart wearable device.

51. The method of any preceding embodiment, wherein a user's identity is authenticated using biometrics.

52. The method of any preceding embodiment, wherein the one or more communications interfaces are selected from the group consisting of a wired communications interface, a wireless communications interface, a cellular communications interface, a WiFi communications interface, a near field communications interface, an infrared communications interface, ZigBee communications interface, a Z-Wave communications interface and a Bluetooth communications interface.

53. The method of any preceding embodiment, wherein access rights to services are provided to the user in the form of a token within the smart wearable device.

54. The method of any preceding embodiment, wherein access rights to services are provided to the user in the form of multiple smart wearable devices.

55. The method of any preceding embodiment, wherein the smart wearable device has a platform selected from the group consisting of hand worn devices, finger worn devices, wrist worn devices, head worn devices, arm worn devices, leg worn devices, ankle worn devices, foot worn devices, toe worn devices, watches, eyeglasses, rings, bracelets, necklaces, articles of jewelry, articles of clothing, shoes, hats, contact lenses, and gloves.

56. The method of any preceding embodiment, further comprising: notifying the authenticated user when their access rights to services have been verified, wherein notification occurs through the output device on the smart wearable device.

57. A system for authenticating a user of a smart wearable device and verifying access rights to services for use with a non-wearable device, the system comprising: (a) a non-wearable device; and (b) a smart wearable device, the device comprising: (i) a housing, wherein the housing encases components of a wearable smart device; (ii) one or more sensors, wherein at least one sensor is a biological sensor configured to acquire biological input; (iii) one or more output devices; (iv) a memory; (v) one or more communications interfaces; (vi) a processor; and (vii) programming residing in a non-transitory computer readable medium, wherein the programming is executable by the computer processor and configured to: authenticate a user's identity; detect a non-wearable device that is in range of the smart wearable device's one or more communications interface verify the authenticated user has access rights to services for use with the non-wearable device; and if access rights are verified, grant access to the services.

58. The system of any preceding embodiment, wherein said programming is further configured to: notify the user when the smart wearable device is out of range for communicating with the non-wearable device, wherein notification occurs through the output device on the smart wearable device.

59. The system of any preceding embodiment, wherein said programming is further configured to: notify the authenticated user when their access rights to services have been verified, wherein notification occurs through the output device on the smart wearable device.

60. The system of any preceding embodiment, wherein access rights to services are provided to the user in the form of a token within the smart wearable device, wherein the token indicates current access rights or expiration of access rights.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A wearable device, the device comprising:
   (a) a housing configured for coupling the wearable device to a first user;
   (b) one or more sensors coupled to the housing, wherein at least one of the one or more sensors is configured for sensing biological or physiological input;
   (c) one or more communications interfaces;
   (d) a processor; and
   (e) programming stored in a non-transitory medium, wherein the programming is readable and executable by the processor, and wherein the programming, when executed, performs steps in companionship wearable tracking for predicting relative relationship health between a pair of companions each wearing one of said wearable device comprising:
      (i) pairing up said wearable device of the first user with a second wearable device of a companion second user, so that information collected by said wearable device is exclusively shared between the pair of companions, said sharing comprising either using direct wireless communication between said wearable device and the second wearable device or intermediated through at least one non-wearable device;
      (ii) sensing and acquiring biological or physiological input through said one or more sensors of said wearable device of a first user;
      (iii) sensing and acquiring proximity data, through said one or more sensors, between said wearable device of the first user and a second wearable device of a second user;
      (iv) identifying the second, companion, wearable device worn by a second user in proximity to said wearable device;
      (v) directly exchanging data with a second communications interface on the second wearable device through said one or more communication interfaces;
      (vi) monitoring and predicting relative intimacy and/or relationship health in response to tracking duration of proximity between said wearable device of the first user and the second, companion, wearable device of the second user;
      (vii) generating visual and/or auditory indications on said wearable device, and its companion wearable device, based on one or more thresholds of the total time spent together over a given period of time.

2. A wearable device as recited in claim 1, wherein the data comprises data relating to the biological or physiological input of the first user, data received about the biological or physiological input of the second user, and data relating to the proximity of the first user with the second user.

3. A wearable device as recited in claim 1, wherein wherein said tracking duration of proximity comprises tracking the total number of hours that the first user is in close proximity to the second user over a given period of time.

4. A wearable device as recited in claim 1, wherein said programming is further configured for said first wearable device generating a notification to the companion second wearable device when the first user is no longer wearing said wearable device, and is also configured to receive notifications from the companion second wearable device if the companion second user is no longer wearing their wearable device.

5. A wearable device as recited in claim 2, wherein the proximity data is stored in said wearable device and configured for collection by the first or second users.

6. A wearable device as recited in claim 2, the programming further configured for:
   sending an output signal to the first user of the second user's proximity to the first user;
   said output signal being one or more of: a vibration, an audible sound, or visible emission.

7. A wearable device as recited in claim 2, wherein the biological or physiological input comprises a signal relating to one or more of the first user's:
   heartbeat, temperature, or blood pressure.

8. A wearable device, the device comprising:
   (a) a housing, wherein the housing encases components of a wearable device;
   (b) one or more sensors, wherein at least one sensor is configured for sensing biological or physiological input;
   (c) one or more communications interfaces;
   (d) a processor; and
   (e) programming stored in a non-transitory medium, wherein the programming is readable and executable by the processor, and wherein the programming, when executed, performs steps in companionship wearable tracking for predicting relative relationship health between a pair of companions each wearing one of said wearable device comprising:
      (i) pairing up said wearable device of the first user with a second wearable device of a companion second user, so that information collected by said wearable device is exclusively shared between the pair of companions, said sharing comprising either using direct wireless communication between said wearable device and the second wearable device or intermediated through at least one non-wearable device;
      (ii) sensing proximity data through said one or more sensors of said wearable device of a first user and a second wearable device of a second user, wherein said wearable device;
      (iii) communicating with the paired second wearable device through said one or more communications interfaces;
      (iv) acquiring one or more permissions relating to data associated with the wearable device or the one or more devices;
      (v) wherein the data comprises application programming associated with the one or more devices; and
      (vi) downloading the application programming from a remote server to the wearable device;
      (vii) monitoring and predicting relative intimacy and/or relationship health in response to tracking duration of proximity between said wearable device of the first user and the second, companion, wearable device of the second user;
      (viii) generating visual and/or auditory indications on said wearable device, and its companion wearable device, based on one or more thresholds of the total time spent together over a given period of time.

9. A wearable device as recited in claim 8, wherein the application programming comprises a subscription service, or a game software or a component thereof.

10. A wearable device as recited in claim 8, wherein said programming is further configured for said first wearable device generating a notification to the companion second wearable device when the first user is no longer wearing said wearable device, and is also configured to receive notifications from the companion second wearable device if the companion second user is no longer wearing their wearable device.

11. A wearable device as recited in claim 8, further comprising:
   one or more environmental sensors coupled to the processor;
   wherein the one or more environmental sensors are configured to sense a physiological or biological characteristic associated with a user of the wearable device.

12. A wearable device as recited in claim 11, wherein acquiring one or more permissions is a function of the one or more environmental sensors sensing a predetermined physiological or biological characteristic of the user; and
   wherein said one or more permissions expire for said wearable device based on a specified time of use, or identification of a second user wearing the device.

* * * * *